United States Patent
Sater

(10) Patent No.: US 9,039,596 B2
(45) Date of Patent: May 26, 2015

(54) SLING ASSEMBLIES FOR TREATING URINARY INCONTINENCE AND METHODS RELATED THERETO

(75) Inventor: Ghaleb Sater, Lynnfield, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 815 days.

(21) Appl. No.: 13/093,473

(22) Filed: Apr. 25, 2011

(65) Prior Publication Data

US 2011/0201877 A1    Aug. 18, 2011

Related U.S. Application Data

(63) Continuation of application No. 12/748,691, filed on Mar. 29, 2010, now abandoned, which is a continuation of application No. 11/229,176, filed on Sep. 19, 2005, now Pat. No. 7,686,759, which is a continuation of application No. 10/025,388, filed on Dec. 19, 2001, now Pat. No. 6,974,462.

(51) Int. Cl.
| | | |
|---|---|---|
| A61F 2/04 | (2013.01) | |
| A61F 2/08 | (2006.01) | |
| A61B 17/04 | (2006.01) | |
| A61B 17/064 | (2006.01) | |
| A61B 17/00 | (2006.01) | |

(52) U.S. Cl.
CPC ........... *A61F 2/0811* (2013.01); *A61B 17/0401* (2013.01); *A61B 17/0642* (2013.01); *A61B 17/0643* (2013.01); *A61B 2017/0046* (2013.01); *A61B 2017/00805* (2013.01); *A61B 2017/0412* (2013.01); *A61B 2017/0414* (2013.01); *A61B 2017/0647* (2013.01); *A61F 2002/0829* (2013.01); *A61F 2002/0864* (2013.01); *A61F 2002/0888* (2013.01)

(58) Field of Classification Search
CPC ..... A61F 2/04; A61F 2/0045; A61B 17/0469; A61B 17/0643; A61B 2017/00805; A61B 2017/0641; A61B 17/068
USPC ............... 600/29–32, 37; 606/151, 28, 72
See application file for complete search history.

(56) References Cited

U.S. PATENT DOCUMENTS

| | | | |
|---|---|---|---|
| 2,825,329 | A | 3/1958 | Caesar |
| 5,500,000 | A | 3/1996 | Feagin et al. |
| 5,720,765 | A | 2/1998 | Thal |
| 5,810,854 | A | 9/1998 | Beach |
| 5,849,019 | A | 12/1998 | Yoon |
| 5,954,057 | A | 9/1999 | Li |
| 6,056,751 | A * | 5/2000 | Fenton, Jr. ............... 606/28 |
| 6,200,330 | B1 | 3/2001 | Benderev et al. |
| 6,273,852 | B1 | 8/2001 | Lehe et al. |
| 6,334,446 | B1 | 1/2002 | Beyar |
| 6,423,080 | B1 | 7/2002 | Gellman et al. |
| 6,506,190 | B1 | 1/2003 | Walshe |
| 6,582,443 | B2 * | 6/2003 | Cabak et al. ............... 606/151 |
| 6,612,977 | B2 | 9/2003 | Staskin et al. |
| 6,638,210 | B2 | 10/2003 | Berger |
| 6,641,524 | B2 | 11/2003 | Kovac |
| 6,641,525 | B2 | 11/2003 | Rocheleau et al. |
| 6,652,450 | B2 | 11/2003 | Neisz et al. |
| 6,689,047 | B2 | 2/2004 | Gellman |

(Continued)

*Primary Examiner* — Christine H Matthews

(57) ABSTRACT

A surgical fastener for use in surgical procedures comprises a first member, a second member, and an anchor. Surgical materials may be secured within the surgical fastener. Methods of securing the surgical fastener to an anatomical structure are disclosed herein.

9 Claims, 16 Drawing Sheets

(56) References Cited

U.S. PATENT DOCUMENTS

| | | |
|---|---|---|
| 6,974,462 B2 * | 12/2005 | Sater ............................. 606/232 |
| 7,686,759 B2 * | 3/2010 | Sater ............................. 600/29 |
| 2002/0082619 A1 | 6/2002 | Cabak |
| 2003/0050530 A1 | 3/2003 | Neisz et al. |
| 2003/0191360 A1 | 10/2003 | Browning |
| 2003/0191480 A1 | 10/2003 | Ulmsten et al. |
| 2004/0111100 A1 | 6/2004 | Benderev et al. |
| 2004/0231678 A1 | 11/2004 | Fierro |
| 2004/0249240 A1 | 12/2004 | Goldmann et al. |

* cited by examiner

SLING ASSEMBLIES FOR TREATING URINARY INCONTINENCE AND METHODS RELATED THERETO

CROSS-REFERENCE TO RELATED APPLICATIONS

This application is a continuation of U.S. application Ser. No. 12/748,691, filed on Mar. 29, 2010, which is a continuation of U.S. application Ser. No. 11/229,176, filed on Sep. 19, 2005, now U.S. Pat. No. 7,686,759, which is a continuation of U.S. application Ser. No. 10/025,388, filed on Dec. 19, 2001, now U.S. Pat. No. 6,974,462, all of which are incorporated herein by reference in their entirety.

TECHNICAL FIELD

This invention generally relates to fasteners used in surgical procedures and more specifically, to fasteners used to secure surgical materials to anatomical structures.

BACKGROUND INFORMATION

Surgical materials such as sutures, slings, and/or patches are anchored to anatomical structures during numerous surgical procedures. In some procedures, the surgeon manipulates the surgical material, such as a sling, to access the anatomical implantation site, threads a suture into the sling and through the anatomical structure, and then knots the suture to secure the sling at the anatomical structure.

In surgical procedures where the anatomical implantation site is difficult to access hand suturing to secure the surgical material to the anatomical implantation site is difficult, if not impossible. Inaccessibility of the anatomical site requires that the suture knot be tied remotely and then slid to the anchoring site. Such anchoring procedures are time consuming and require surgical skill. Insufficient knot tension and improper knot positioning risks improperly secured surgical material.

In other surgical procedures, surgical anchors are used to secure surgical materials at the implantation site. In such applications, a suture is threaded through an eyelet disposed through a surgical anchor and the suture secures the surgical material to the surgical anchor. In such procedures, the surgical material may be attached to the surgical anchor via a suture before or after the anchor is affixed to the anatomical structure. Alternatively, the surgical material is positioned inside the body of a patient, and a surgical anchor is pierced just through the surgical material and then into the anatomical site to anchor the surgical material into the anatomical implantation site.

If a fastener is used to anchor surgical material to anatomical structures, fasteners can generally require multiple steps in order to secure the surgical material to the implantation site. Some fasteners require positioning the material and suturing the material at the site of attachment to the anatomical structure. Other fasteners require the surgeon to manipulate the surgical material to the appropriate position inside the body of the patient and then pierce or otherwise attach the material to the anatomical structure using the fastener.

Thus, current surgical methods require surgeons to employ multiple steps to implant surgical material at the anatomical implantation site. Eliminating surgical steps increases the speed at which surgical procedures are performed which in turn reduces the length of time during which the patient is under anesthesia. Furthermore, decreasing the number of surgical steps reduces the operating room time required for the surgery, providing improved patient care as well as economic advantages.

SUMMARY OF THE INVENTION

The present invention relates to surgical fasteners that eliminate a surgical step that requires a surgeon to secure material to be implanted in a patients body, to a fastener while working inside the body of the patient. The instant invention is a surgical fastener that enables surgeons to secure surgical material to a fastener prior to commencing surgery, and then to anchor only the surgical fastener within the patient during surgery.

The surgical fastener according to the invention also reduces the variability in surgical anchoring associated with insufficient knot tension and improper positioning caused by difficult anchoring site accessibility and surgeon skill level variability. The surgical material according to the invention may be introduced into areas of the body that are difficult to access and anchored within the patient. The surgical materials according to the invention are pre-attached to the anchor obviating the need by the surgeon to attach the surgical materials to the anchor at the implantation site.

The present invention relates to a surgical fastener featuring a first member and a second member and an anchor. The method also relates to methods of securing the surgical fastener to an anatomical structure.

In general, in one aspect, the surgical fastener features a first member and a second member, the first member has a proximal end and a distal end and the first member defines at least a first interior face and a first exterior face extending therebetween. The first member includes a first engagement element. The second member has a proximal end and a distal end and the second member defines at least a second interior face and a second exterior face extending therebetween. The second member includes a second engagement element. The first engagement element and the second engagement element are capable of engaging to fix the first interior face and the second interior face in proximity. In some embodiments, the second engagement element fits and mates with the first engagement element. The surgical fastener includes an anchor to secure the first member and second member to an anatomical structure.

In some embodiments, the anchor also is disposed on the first interior face of the first member and is the first engagement element and an aperture disposed through the second member is the second engagement element. The surgical fastener is placed in the closed position when the anchor passes through the aperture. In other embodiments of the surgical fastener, the anchor is disposed on an exterior face of the first member or the second member of the surgical fastener. The anchor may be secured to anatomical structures such as, for example, bone, cartilage, tissue, muscle, and ligament.

Embodiments of the invention also include surgical fasteners in which an anchor is not integral with the first member or the second member. In one embodiment, the first member defines a first aperture extending therethrough and the second member defines a second aperture extending therethrough and the first and second apertures may be positioned to define an opening through the first member and the second member of the surgical fastener. When the surgical fastener is placed in a closed position the opening defined through the first member and the second member permits an anchor to pass through the surgical fastener. In one embodiment, the anchor includes a tapered head, a shank, and a base. In yet another embodiment, the anchor is attached to the fastener by a flexible tether. In one embodiment, a hinge attaches the first member and the second member. The anchor may be freely attached to the surgical fastener by piercing the flexible tether through the hinge. Alternatively, a surgical fastener comprising a first member, a second member, and a hinge may hold a flexible tether between the interior face of the first member and the interior face of the second member.

Further, the first member and the second member may include one or more first engagement element and one or more mating second engagement element. Exemplary first and second engagement elements include: a pin and a blind hole, a pin and an aperture, and a ridge and a groove that are disposed on the first member and the second member of the surgical fastener, respectively. In some embodiments, the distal end of the first member has a first engagement element tongue and the distal end of the second member has a second engagement element notch. In one embodiment, the first member and the second member have a substantially similar size and/or configuration.

When the first member and the second member are properly oriented so that the first engagement element and the second engagement element couple, the surgical fastener is coupled and positioned in the closed position. In one embodiment, the surgical fastener is irreversibly coupled, i.e., the first member and the second member are maintained in proximity and in the closed position.

In general, in another aspect, the invention features a surgical fastener system that includes at least one surgical fastener including an anchor and having a first member and a second member and a surgical material. The surgical material is secured within the surgical fastener. The surgical material is selected from the group consisting of slings, sutures, meshes, yarns, tapes, threads, grafts, fabrics, and sheaths.

In yet another aspect, the invention features a method of securing a surgical fastener system of an anatomical structure. According to the method, the surgical fastener system is releasably attached to a surgical implantation device, the surgical fastener is introduced to an anatomical structure implantation site. The surgical fastener is anchored to the anatomical structure implantation site.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 1A:
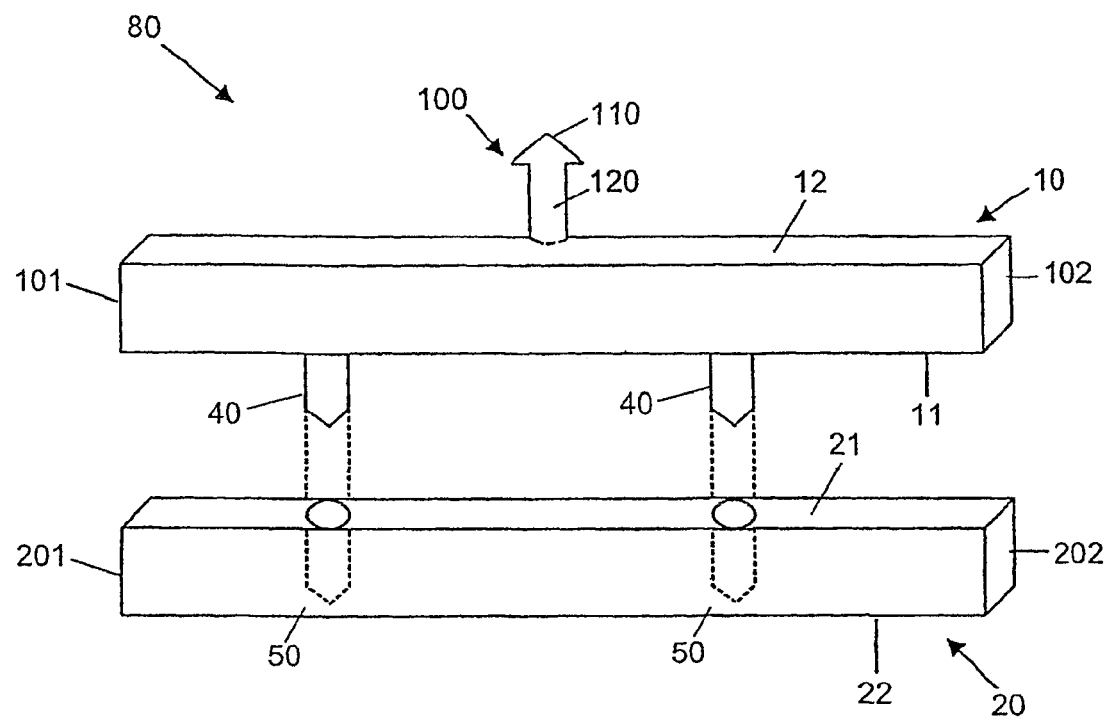
FIG. 1A illustrates a plan view of one disclosed embodiment of a surgical fastener with an integral anchor in accordance with the present invention.

The present invention depends, in part, upon the recognition that methods for attaching surgical materials known in the art are time consuming and that the efficacy of these methods are subject to variable surgical skill level. Thus, the present invention provides for improved surgical anchor attachment devices, as well as methods that employ such devices.

DEFINITIONS

In order to more clearly and concisely point out the subject matter of the claimed invention, the following definitions are provided for specific terms which are used in the following written description and appended claims.

Anatomical structure. As used herein, the term "anatomical structure" means any macroscopic structure comprising all or a portion of a tissue or organ within the body of an animal. Examples include but are not limited to bone, cartilage, tissue, muscle, fascia and ligament.

Anchor. As used herein, the term "anchor" means a surgical suture, tape, tack, screws, nails, staple, steak, other tissue piercing devices or a similar device used to securely attach surgical materials to an anatomical structure.

Aperture. As used herein, the term "aperture" means a hole in an object that extends through the object from one surface of the object to another surface of the object and is visible from at least two surfaces of the object.

Blind hole. As used herein, the term "blind hole" means a hole in an object that does not extend through the object and is only visible from one surface of the object.

Coupling. As used herein, with respect to a first engagement element and a second engagement element, the term "coupling" means complementary shapes, shaped with respect to each other such that when placed in proximity or pushed together the first engagement element and the second engagement element join or mate, i.e., fit together. Examples of coupling first and second engagement elements include a pin and a blind hole; a pin and an aperture; a tongue and a notch; a ridge and a groove.

Detachable surgical anchor implantation device. As used herein, the term "detachable surgical anchor implantation device" means an instrument that releasably engages a surgical anchor and detaches from the anchor after implantation or insertion of the anchor in an anatomical structure.

Engagement element. As used herein, the term "engagement element" means an element that can interlock and mesh with a mating engagement element.

Flexible tether. As used herein, the term "flexible tether" means a line, suture, thread, lead or restraint that may be attached to an object and may be moved from site to site.

Implantation site. As used herein, the term "implantation site" means the location inside the body of the patient where the anchor attached to the surgical fastener is secured.

Integral. As used herein, the term "integral" means formed as a unit or joined to form a single integrated unit.

Surgical material. As used herein, the term "surgical material" means a physical object that is secured to an anatomical structure at an implantation site during surgery. Such surgical materials include but are not limited to slings, sutures, meshes, yarns, tapes, threads, grafts, fabrics, and sheaths.

General Considerations

Generally, the surgical fastener of the present invention includes a first member and a second member and an anchor. Also, the surgical fastener may comprise one or more engagement elements that secure a surgical material within the surgical fastener. In some embodiments of the present invention, the engagement element secures the first member and the second member of the surgical fastener in the closed position. In an alternative embodiment, the anchor performs some or all of multiple functions: it is the engagement element that secures surgical materials within the surgical fastener, it maintains the first member, and the second member of the surgical fastener in the closed position, and it anchors the fastener to an anatomical structure. The surgical fastener is secured to the desired anatomical structure by driving the anchor of the surgical fastener into the anatomical structure to attach the surgical fastener to the target anatomical structure. Surgical fasteners may be employed in a plurality of surgical procedures, for example, urinary incontinence, tissue approximation, and vessel occlusion.

Methods employing the present invention enable surgeons to secure surgical material inside the body of a patient in fewer steps then other procedures thus reducing the time required for the surgery. Specifically, methods of the invention eliminate the surgical steps that require a surgeon to first manipulate and position the surgical material, and then, second, to secure the material at the implantation site within the patient's body. Surgeons may use the present invention to secure surgical material within a surgical fastener system, prior to commencing surgery. According to the invention, the surgeon needs only to anchor the surgical fastener system at the anatomical implantation site during surgery, eliminating the first step of manipulating and positioning the surgical material, thereby simplifying and reducing the time required for the surgical procedure.

Surgical Fastener

Referring to FIG. 1A, an embodiment of a surgical fastener 80 in accordance with the present invention is illustrated. The surgical fastener 80 includes a first member 10 and a second member 20.

The first member 10 has a proximal end 101 and a distal end 102. The first member 10 includes a first interior face 11 and a first exterior face 12. The second member 20 includes a second interior face 21 and a second exterior face 22. In one embodiment according to the invention, an anchor 100 is integral to the first exterior face 12 of the first member 10. Alternatively, the anchor 100 can be fixed to the second exterior face 22 of the second member 20. The anchor 100 on the first exterior face 12 may be disposed on the proximal end 101, the distal end 102, or anywhere therebetween.

As shown in FIG. 1A, in one embodiment the anchor 100 is attached near the midpoint between the proximal end 101 and the distal end 102 of the first exterior face 12 of the first member 10. In one embodiment, the anchor 100 has a shank 120 and a tapered head 110. One end of shank 120 is integral with the first exterior face 12 of the first member 10. The second end of shank 120 extends beyond the first exterior face 12 of the first member 10. The tapered head 110 is positioned at the second end of the shank 120. In alternative embodiments, the anchor may be formed as a cylinder, a screw, a staple, a steak, or in any other form of attachment device known in the surgical arts.

Referring still to FIG. 1A, in one embodiment according to the invention, the first interior face 11 of first member 10 has at least a first engagement element 40. The second interior face 21 of second member 20 has a second engagement element 50. When first member 10 and second member 20 of surgical fastener 80 are placed in proximity and properly oriented, the first engagement element 40 and the second engagement element 50 are aligned so that first engagement element 40 and second engagement element 50 couple. When the first member 10 and the second member 20 are properly oriented so that at least the first engagement element 40 and second engagement element 50 couple, the surgical fastener 80 transitions from the open position to the closed position. In some embodiments, when the surgical fastener 80 is coupled, the surgical fastener 80 is irreversibly maintained in the closed position. One or more first engagement element 40 may be positioned on the interior face 11 of the first member 10, and a corresponding number of complementary second engagement element(s) 50 may be present on the interior face 21 of second member 20 of the surgical fastener 80.

Figure 1B:
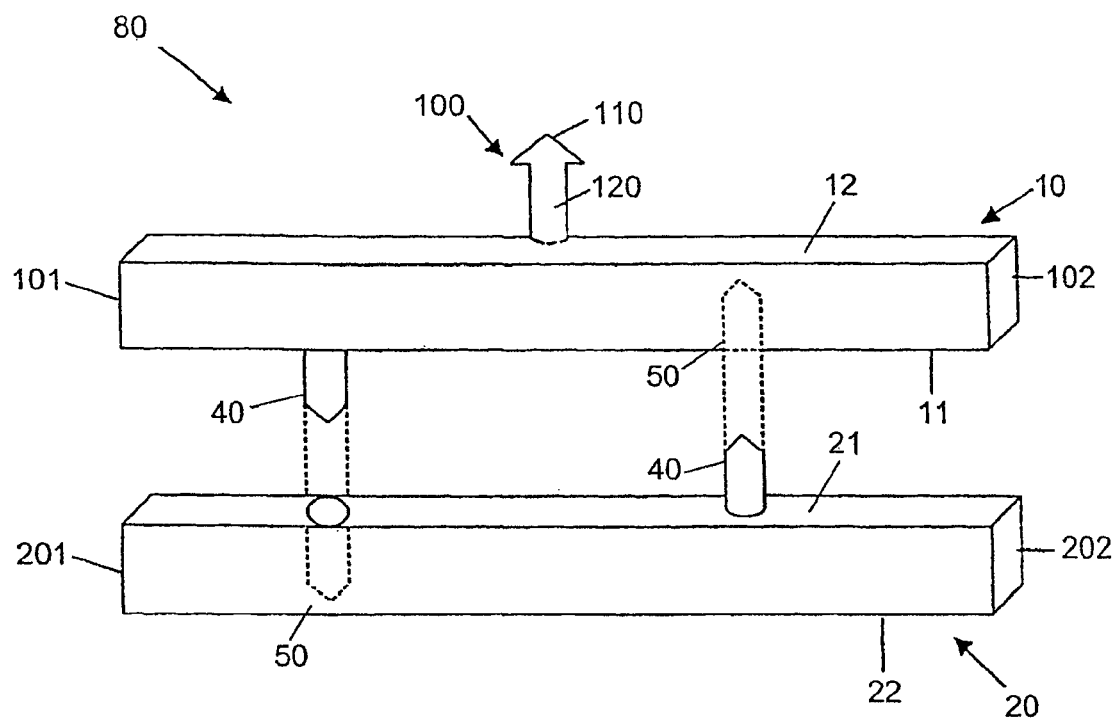
FIG. 1B illustrates a plan view of another embodiment of a surgical fastener with integral anchor including a first engagement element pin and a second engagement element blind hole, in accordance with the present invention.

Optionally, a first engagement element 40 and a second engagement element 50 may be placed on the same member 20 of the surgical fastener 80. For example, as shown in FIG. 1B, both a first engagement element 40 and a second engagement element 50 may be placed on the first interior face 11 of first member 10. Also, a coupling second engagement element 50 and first engagement element 40 may be placed on the second interior face 21 of the second member 20. When the first member 10 and the second member 20 are properly oriented so that the complementary first engagement element 40 and second engagement element 50 on each member couple, the first member and the second member surgical fastener 80 may be engaged and thus placed in the closed position. In one embodiment, the first member 10 and the second member 20 have a substantially similar size and/or configuration.

Generally, the dimensions of the first engagement element 40 and the second engagement element 50 are selected according to the dimensions of the surgical material to be secured by the surgical fastener 80. For example, surgical fastener 80 may be used to attach a suburethral sling to the pubic bone of a female patient to treat urinary incontinence. Such a surgical fastener 80 may employ one or more first engagement elements, for example, pins 40 measuring in the range of 1 cm to 4 cm, preferably 2 cm in length, from where the pin is disposed on the first interior face 11, the pin having a diameter in range of about 0.125 cm to 0.5 cm, preferably, 0.25 cm. In a surgical application where the device is employed to attach, for example, an artificial ligament, the pin 40 will be appropriately shaped and sized for the application where it is used.

Figure 1C:
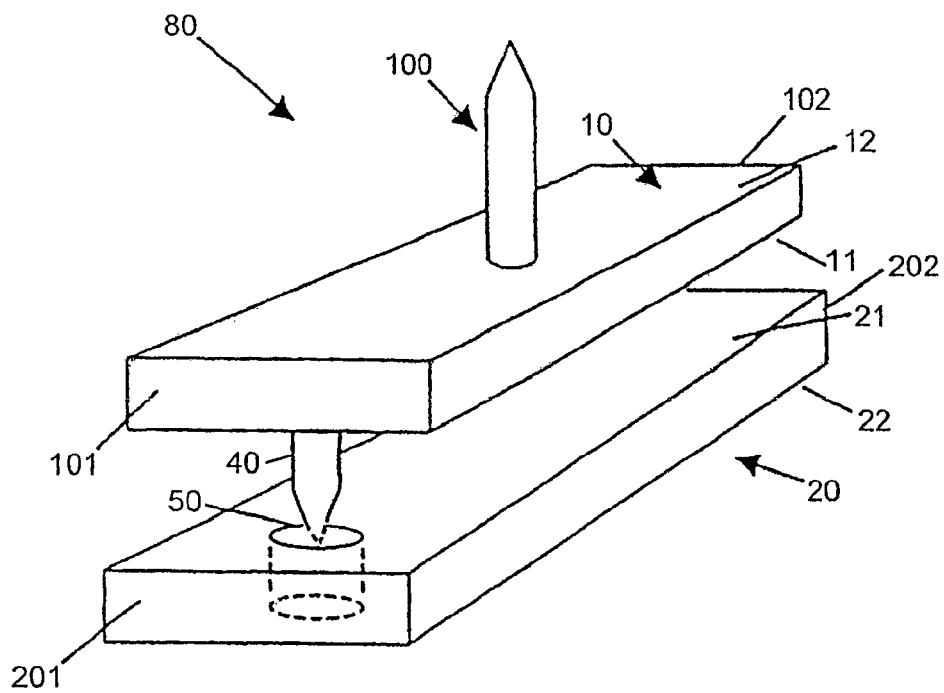
FIG. 1C illustrates a plan view of another embodiment of a surgical fastener with integral anchor including a first engagement element pin and a second engagement element aperture, in accordance with the present invention.

FIG. 1C provides an alternative embodiment of the surgical fastener 80 of the invention. In this embodiment, one or more first engagement elements 40 are attached to the first interior face 11 of first member 10. One or more second engagement elements 50 are defined by the second member 20 positioned on the second interior face 21. For example, one or more apertures 50 extend through the second member 20 from the second interior face 21 through to the second exterior face 22. The position and dimensions of one or more pins 40 are chosen to be complementary to the apertures 50. The dimensions of an aperture 50 may have a larger diameter then the pin 40, for example, as shown in FIGS. 1C through 1F. Alternatively, the dimensions of the second engagement element 50 may be designed to be close to the dimensions of the first engagement element 40 such that when coupled the first engagement element and the second engagement element fit one another closely.

Figure 1D:
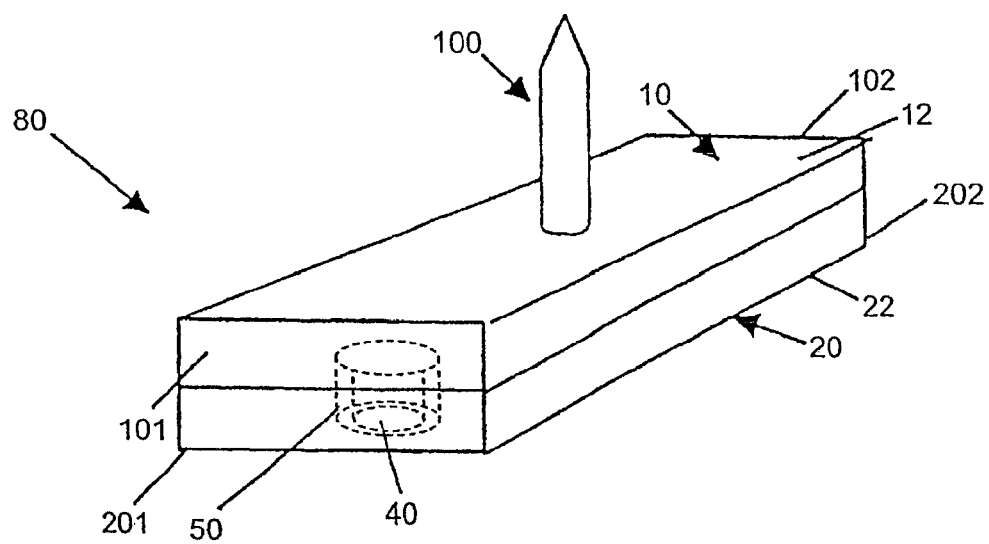
FIGS. 1D to 1F illustrate various embodiments of the first engagement element pin and second engagement element aperture illustrated in FIG. 1C.
Figure 1E:
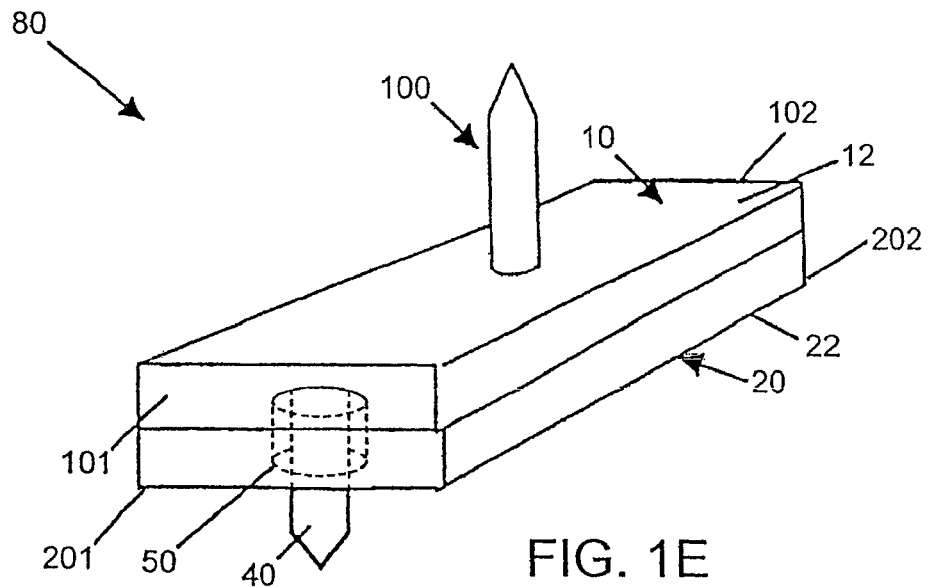
Figure 1F:
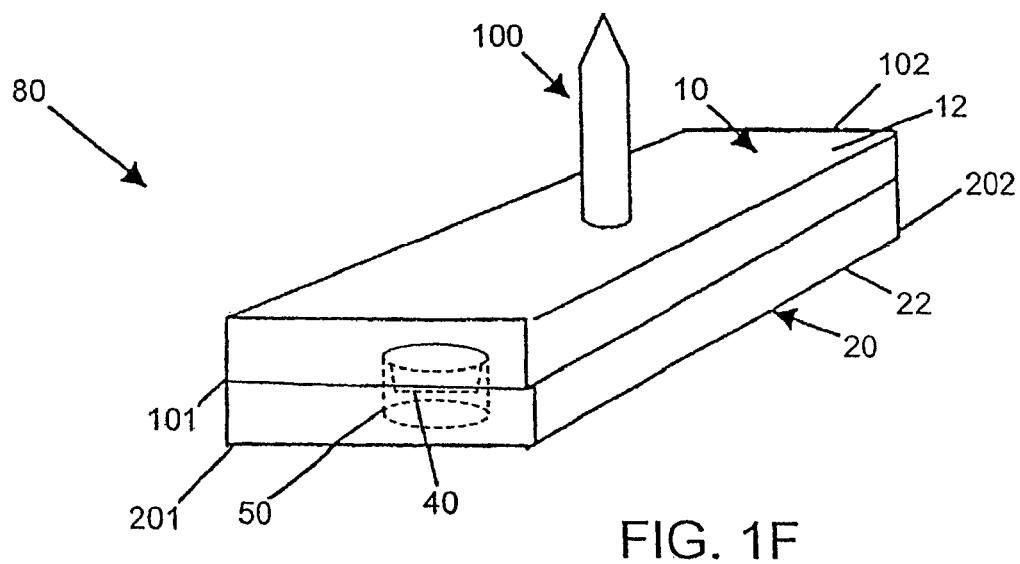
Figure 1G:
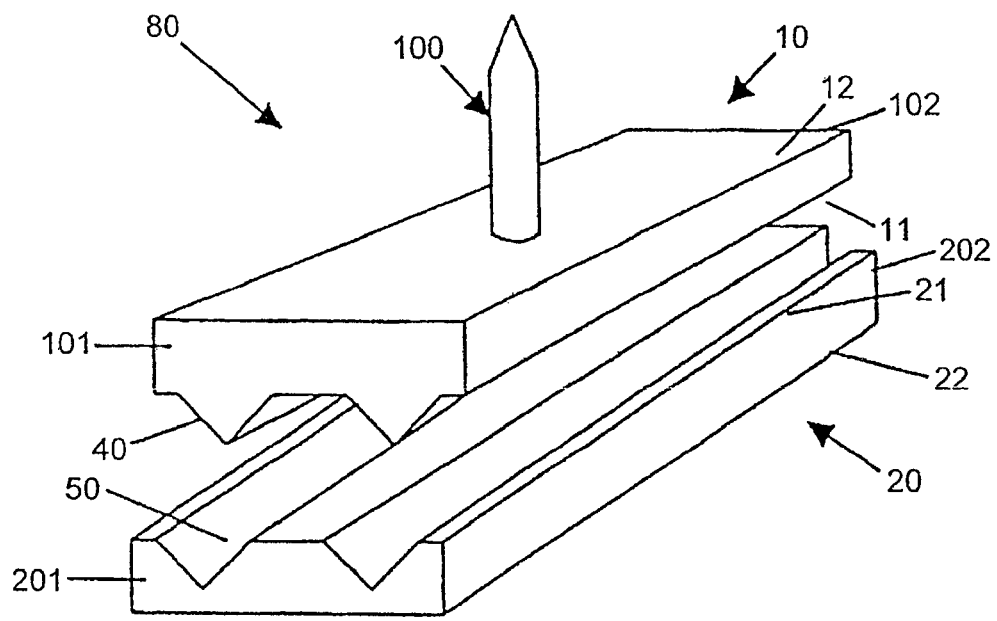
FIG. 1G illustrates a plan view of another embodiment of a surgical fastener with integral anchor including a first engagement element ridge and a second engagement element groove, in accordance with the present invention.

Referring to FIGS. 1C to 1F, when the first member 10 and the second member 20 are in proximity and alignment and surgical fastener 80 is placed in the closed position, the pin 40 extends through the second engagement element, aperture 50. The pin 40 may extend all the way through aperture 50 and be flush with the second exterior face 22 as illustrated in FIG. 1D. Alternatively, the pin 40 may extend beyond the second exterior face 22 and protrude beyond the second exterior face 22 as illustrated in FIG. 1E. In yet another embodiment, the pin 40 may extend part way through aperture 50 leaving a portion of aperture 50 unfilled, as illustrated in FIG. 1F. In some embodiments, the aperture 50, as shown in FIGS. 1D to 1F, may be designed to couple with the pin 40 so that the dimensions of pin 40 and the dimensions of aperture 50 are close.

Figure 1H:
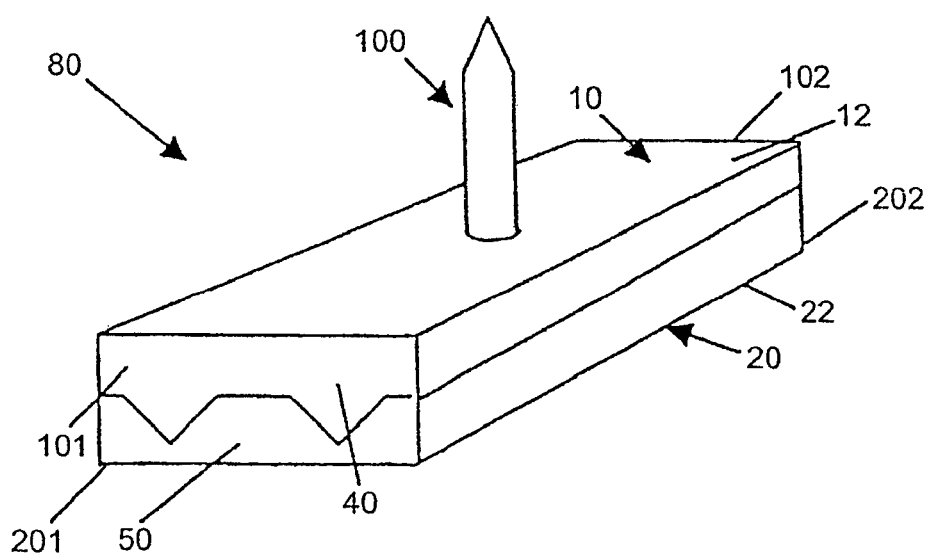
FIG. 1H illustrates a plan view of an embodiment of the surgical fastener illustrated in FIG. 1G in the closed position.

In another embodiment according to the invention, illustrated in FIG. 1O, the first engagement element 40 includes one or more ridges on the first interior face 11 of first member 10. The second engagement element 50 includes one or more grooves complementary to the ridges 40 positioned on the second interior face 21 of the second member 20. When the first member 10 and the second member 20 of the surgical fastener 80 are placed in proximity and properly oriented, the first engagement element 40 ridge and the second engagement element 50 groove are aligned so that ridge 40 and groove 50 couple. As illustrated in FIG. 1H, when the first member 10 and the second member 20 are properly oriented so that the first engagement element 40 and the second engagement element 50 couple, the surgical fastener 80 transitions from the open position to the closed position. One or more first engagement element ridge(s) 40 may be positioned on the interior face 11 of the first member 10 and a corresponding and complementary number of second engagement element grooves 50 may be present on the second interior face 21 of the second member 20 of the surgical fastener 80. The position size and shape of the grooves 50 are complementary to the size and shape of the ridges 40. In some embodiments the dimensions of the ridge(s) 40 and groove(s) 50 are close and each ridge 40 and groove 50 couple closely.

Generally, the dimensions of the first engagement element ridge 40 and the second engagement element groove 50 are selected according to the dimensions of the surgical material to be secured by the surgical fastener 80. In one embodiment, each ridge 40 disposed on the interior face 11 of the first member 10 of surgical fastener 80 has the same dimension. Alternatively, the interior face 11 of the first member 10 of the surgical fastener 80 may include ridges 40 that have different dimensions. The dimensions of ridge 40 and groove 50 will be selected according to the surgical application and surgical material that is being secured by the surgical fastener 80. For example, the ridge 40 of the surgical fastener 80 employed to treat female urinary incontinence may have a length in the range of 1 cm to about 4 cm, preferably 2 cm in length. The greatest thickness of the ridge, measured from the first interior surface 11 of the first member 10, may measure in the range of 0.5 cm to about 1 cm long, preferably 0.75 cm in length. The groove 50 may be complementary to the size and shape of the ridge 40 such that when the ridge 40 and groove 50 are placed in proximity and properly oriented, the ridge 40 and the groove 50 are coupled. When the ridge 40 and groove 50 are coupled, the surgical fastener 80 is in the closed position.

Figure 1I:
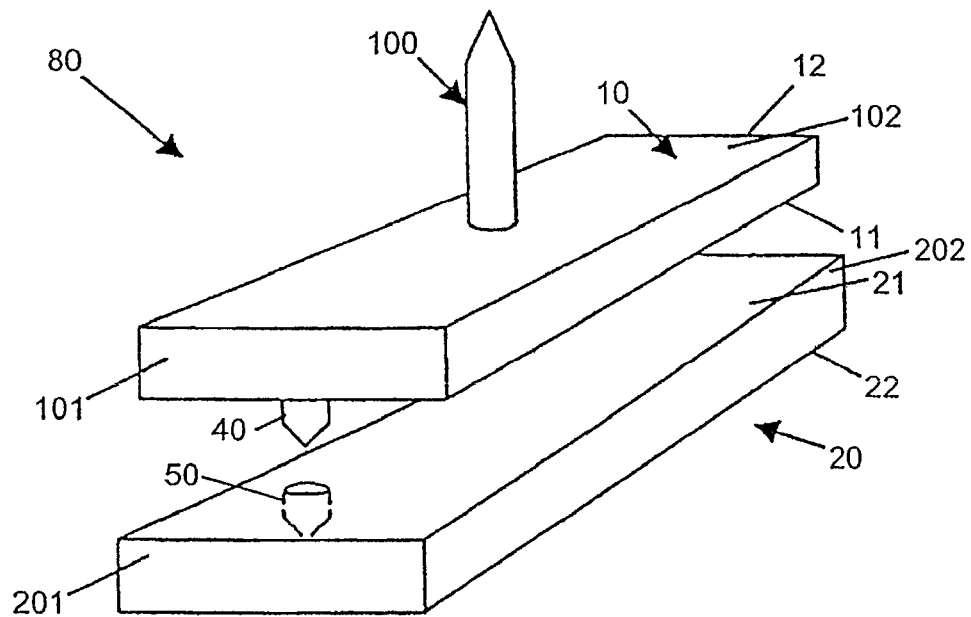
FIG. 1I illustrates a plan view of another embodiment of a surgical fastener with integral anchor including a first engagement element pin and a second engagement element blind hole, in accordance with the present invention.

As shown in FIG. 1I, in one embodiment according to the invention, the first engagement element 40 comprises one or more pins attached to the first interior face 11 of first member 10. The second engagement element 50 comprises one or more blind holes defined by second member 20 positioned on the second interior face 21 of second member 20. The blind hole 50 does not extend through the second member 20 but, rather, forms a cavity.

Figure 1J:
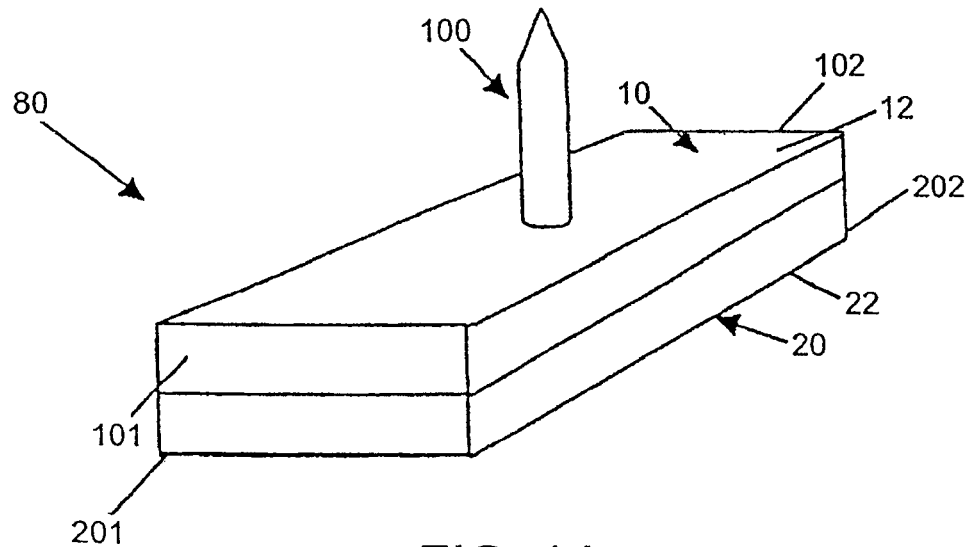
FIG. 1J illustrates a plan view of an embodiment of the surgical fastener illustrated in FIG. 1I in the closed position.

When the first member 10 and the second member 20 of the surgical fastener 80 move from the open position, illustrated in FIG. 1I, and are placed in proximity and properly oriented, the first engagement element pin 40 and the second engagement element blind hole 50 are aligned so that the pin 40 enters the blind hole 50. The pin 40 and blind hole 50 are coupled such that the surgical fastener 80 has transitioned from the open position to the closed position, illustrated in FIG. 1J. Referring again to FIG. 1I, in one embodiment according to the invention, one or more first engagement elements 40 may be positioned on the interior face 11 of the first member 10, and a corresponding number of complementary second engagement elements may be present on the interior face 21 of the second member 20 of the surgical fastener 80. The position and dimensions of pin 40 are chosen to be complementary to the depth of blind hole 50. For example, a surgical fastener 80 used to attach a suburethral sling to the pubic bone of a female patient to treat urinary incontinence may employ one or more pins 40 measuring in the range of 1 cm to 5 cm, preferably 2 cm in length, from where the pin 40 is disposed on the first interior face 11, the pin 40 having a diameter in range of about 0.125 cm to 0.5 cm, preferably, 0.25 cm. In a surgical application where the device is employed to attach, for example, an artificial ligament, the pin 40 will be appropriately shaped and sized for the application where it is used.

Figure 2A:
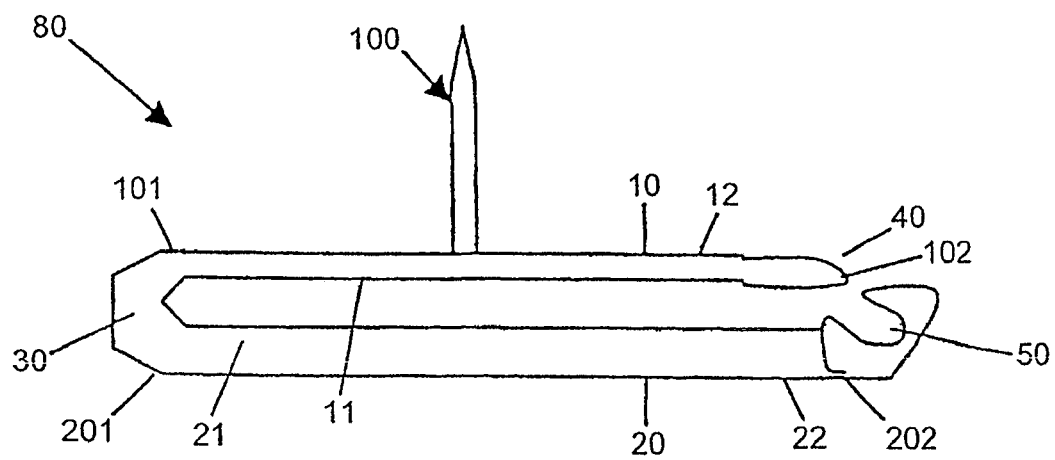
FIG. 2A illustrates a longitudinal section of another embodiment of a surgical fastener with integral anchor including a hinge and a first engagement element tongue and a second engagement element notch, in accordance with the present invention.

FIG. 2A illustrates another embodiment of a surgical fastener 80 including a first member 10, a second member 20, and a hinge section 30. The surgical fastener 80 also features an anchor 100 attached to the first exterior face 12 of first member 10. The hinge section 30 joins the proximal end 101 of first member 10 to the proximal end 201 of second member 20. The distal end 102 of the first member 10 features a tongue 40. A notch 50 capable of coupling with the tongue 40 is positioned at the distal end 202 of the second member 20.

Referring to FIG. 2A, the surgical fastener is in the open position when the first member 10 and the second member 20 are aligned and placed in proximity, the hinge section 30 is compressed bringing together the first interior face 11 of the first member 10 and the second interior face 21 of the second member 20. FIG. 28 illustrates the surgical fastener 80 in the closed position. When the hinge 30 is compressed, the tongue 40 is pushed into and is coupled with the notch 50 fixedly attaching the tongue 40 into the notch 50.

Figure 2B:
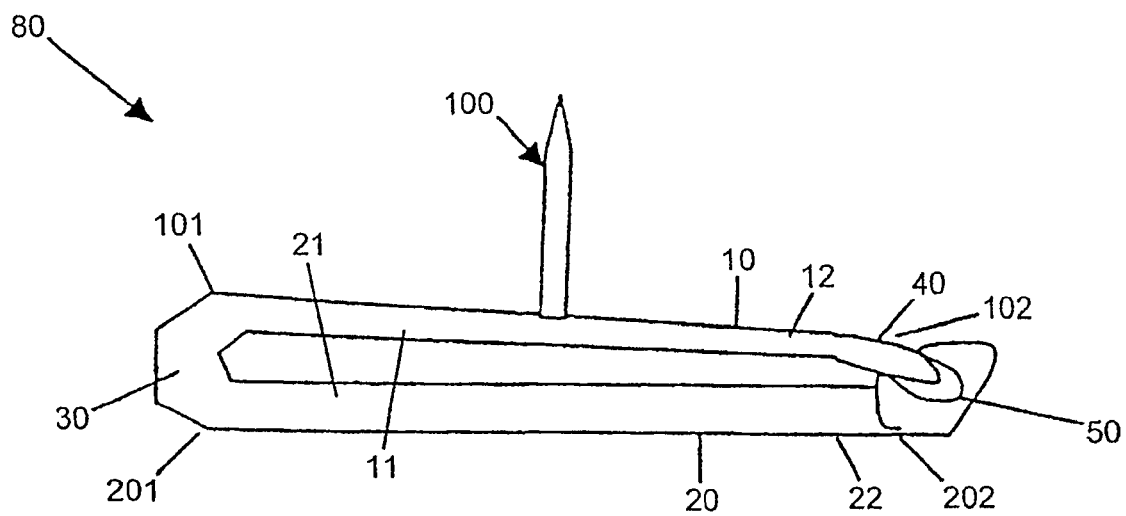
FIG. 2B illustrates the surgical fastener of FIG. 2A in the closed position.
Figure 2C:
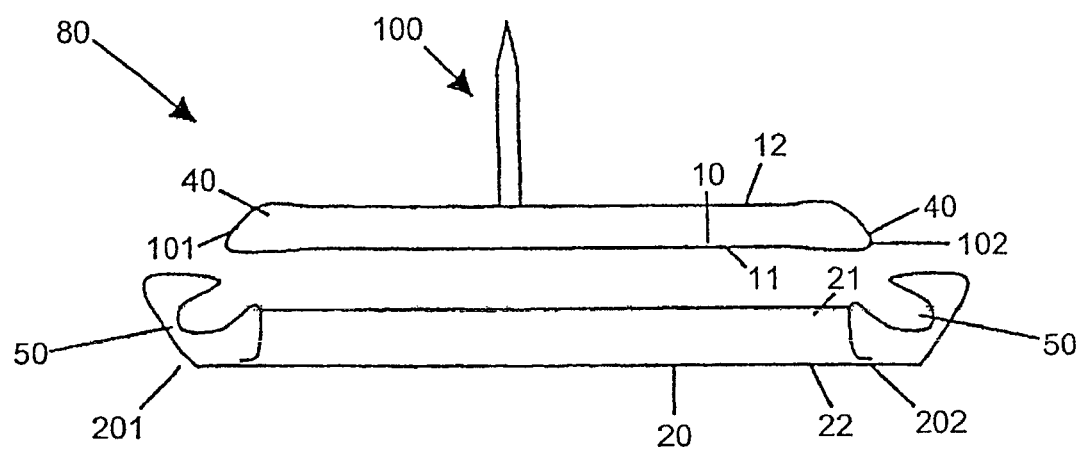
FIG. 2C illustrates the another embodiment of a surgical fastener with integral anchor including at least one first engagement element tongue and at least one second engagement element notch, in accordance with the present invention.

In an alternative embodiment, illustrated in FIG. 2C, the tongue 40 is located at the distal end 102 of the first member 10 and the notch 50 is present at the distal end 202 of the second member 20. At least a second tongue 40 and a complementary notch(s) 50 are also present at the proximal end 101 of the first member 10 and proximal end 201 of second member 20, respectively. The first member 10 and the second member 20 are properly oriented so that the tongue 40 present at the distal end 102 of the first member 10 and the corresponding complementary notch present at the distal end 202 of the second member 20 and the tongue 40 present at the proximal end 101 of the first member 10 and the corresponding complementary notch present at the proximal end 201 of the second member 20 align. Pushing the proximal ends and the distal ends of the first member 10 and second member 20 together so that each complementary tongue 40 and notch 50 couple transitions the surgical fastener 80 from the open position to the closed position. Surgical fastener 80 may be maintained in the closed position by the coupled tongue 40 and notch 50 at the distal and proximal ends of the members of surgical fastener 80.

In yet another embodiment (not shown) of the surgical fastener 80, the distal end 102 of first member 10 may have a tongue 40 and the first member 10 proximal end 101 may have a notch 50. The distal end 202 of second member 20 has a notch 50, the notch 50 has dimensions complementary to the tongue 40 that is on the distal end 102 of first member 10. Similarly, the proximal end 201 of second member 20 has a tongue 40 that couples with the notch 50 that is on the proximal end 101 of first member 10. When the first member 10 and the second member 20 of surgical fastener 80 are placed in proximity and properly oriented, the tongue 40 and notch 50 on each member are aligned, then each tongue 40 and notch 50 are coupled and the surgical fastener 80 transitions into the closed position from the open position.

Figure 2D:
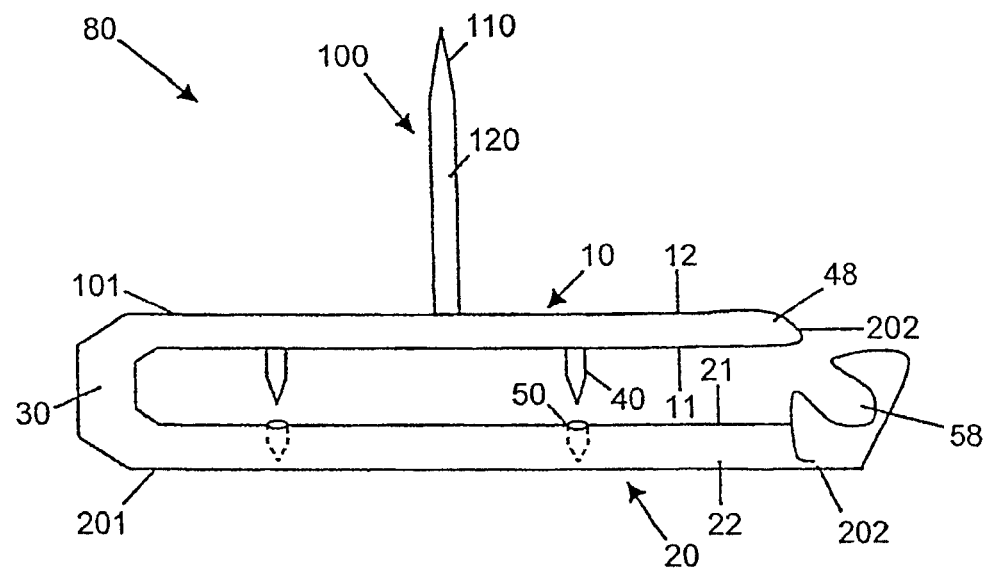
FIG. 2D illustrates a longitudinal section of another embodiment of a surgical fastener with integral anchor including a hinge and a first engagement element tongue and a second engagement element notch and also including a first engagement element pin and second engagement element blind hole, in accordance with the present invention.

As shown in FIG. 2D, the surgical fastener 80 with integral anchor 100 depicted and described in association with FIGS. 2A and 2B, may further include at least one first engagement element 40 and at least one second engagement element 50. When the interior face 11 of the first member 10 and the interior face 21 of the second member 20 are moved toward one another, the first engagement element pin 40, attached to the first interior face 11, couples with the second engagement element blind hole 50, positioned on the second interior face 21. Thus, in this embodiment, the surgical fastener 80 is in the closed position when the mating tongue 40 and notch 50 are coupled and the first engagement element pin 40 and the second engagement element blind hole 50 also couple.

The first member 10, second member 20, hinge section 30, first engagement element 40, second engagement element 50, and anchor 100 may each be made of material selected from a group of permanent and non-bio absorbable materials. Such permanent and non-bioabsorbable materials include acetal homopolymers or copolymers, polyethylene, polypropylene, polycarbonate or Acrylonitrile Butadiene Styrene (ABS) and surgical grade metals; for example, titanium or stainless steel. Alternatively, each part of the surgical fastener 80 may be composed of material selected from a group of materials that are gradually absorbed by the body. Such materials include polyglycolic acid, polyactic acid and trimethylene carbonate copolymers.

Figure 3A:
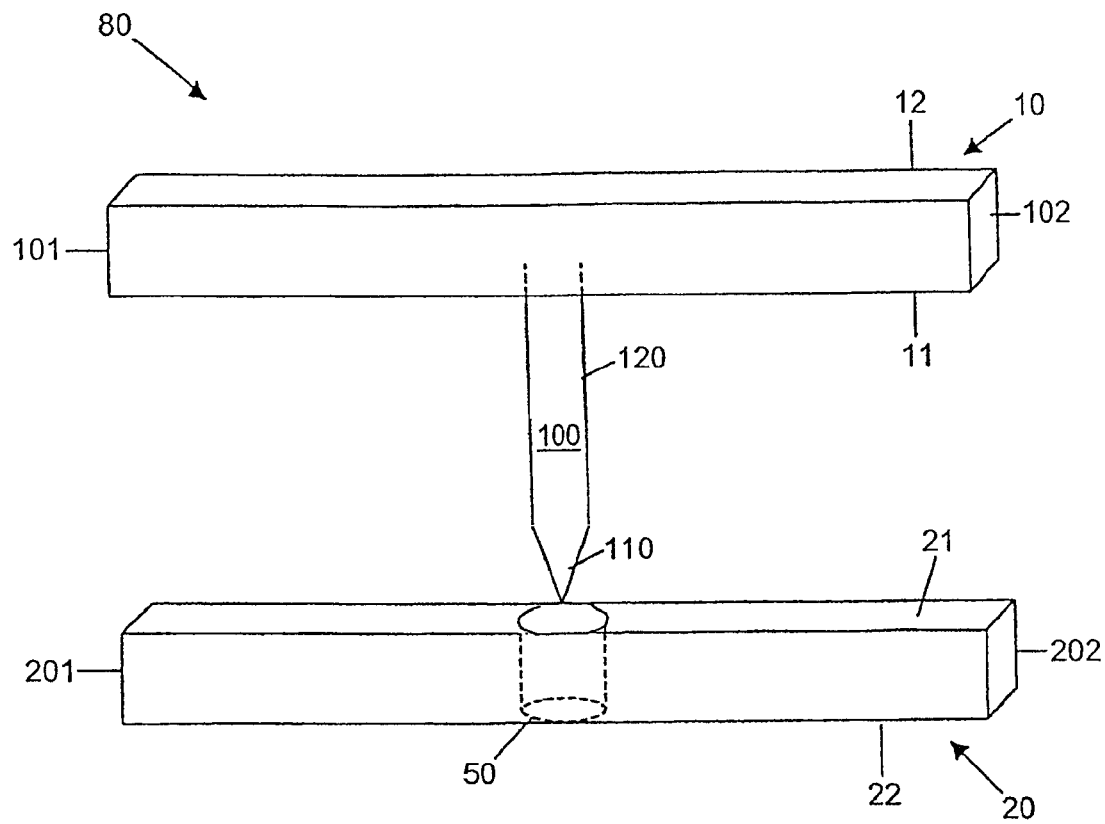
FIG. 3A is a plan view of the open position of another embodiment of a surgical fastener with integral anchor in which the integral anchor provides a first engagement element and the second engagement element is an aperture, in accordance with the present invention.
Figure 3B:
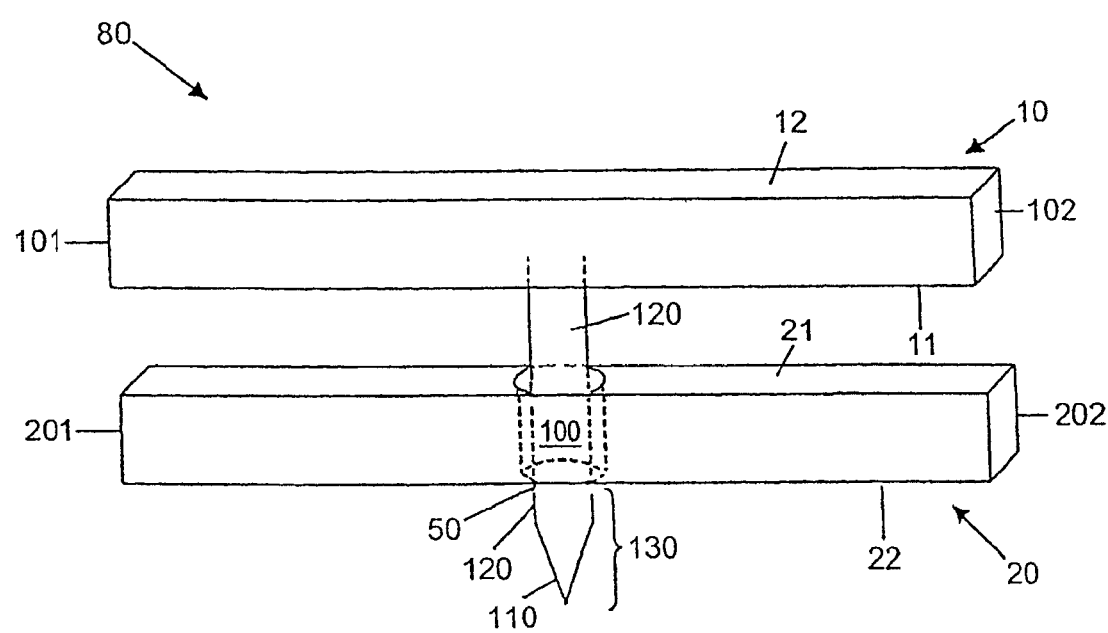
FIG. 3B is a plan view of the closed position of the surgical fastener illustrated in FIG. 3A.

FIG. 3A is a schematic view of another embodiment of a surgical fastener 80 comprising a first member 10, a second member 20, and an anchor 100 in the open position of surgical fastener 80. The anchor 100 is attached to the first interior face 11 of the first member 10. An aperture 50 extends through the second member 20 from the first interior face 21 to the second exterior face 22. Aperture 50 is configured to allow the tapered head 110 and the shank 120 of anchor 100 to pass through the second member 20 beyond the exterior face 22 of second member 20. Referring to FIG. 3B, in the second position of surgical fastener 80, the closed position, the first member 10 and the second member 20 are aligned and placed in proximity, an anchor 100 extends through the aperture 50, the aperture 50 extends through the second member 20. The surgical fastener 80 is coupled when the anchor 100 extends through aperture 50. The portion 130 of anchor 100 that extends beyond the second exterior face 22 can be utilized to anchor the surgical fastener 80 to an anatomical structure. The portion 130 of the anchor 100 that extends beyond the second exterior face 22 includes some or all of tapered head 110 and may include some of shank 120.

Figure 3C:
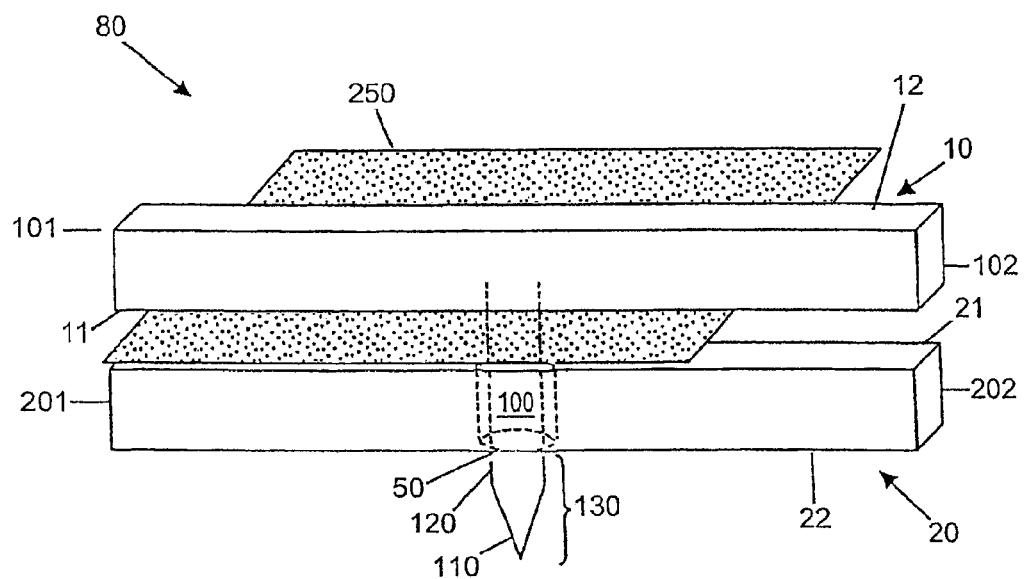
FIG. 3C is a plan view of the surgical fastener system where the surgical fastener illustrated in FIG. 3A is in the closed position and surgical material is held by the surgical fastener.

Referring still to FIGS. 3A and 3B in one embodiment according to the invention, the anchor 100 serves dually as an anchor for attaching surgical materials to an anatomical structure and as the first engagement element 40. The anchor 100 and the aperture 50 maintain the surgical fastener 80 in the closed position illustrated in FIG. 3B when it is secured to an anatomical structure described below. Referring to FIG. 3C, in one embodiment, the anchor 100 pierces the surgical material 250 held within the surgical fastener 80 and then extends through the second member 20. Alternatively, the surgical material 250 may also include an aperture (not shown) configured such that the anchor 100 passes therethrough and the surgical material 250 is not pierced by the anchor 100. In yet another embodiment of the invention, the surgical material 250 may be positioned within the surgical fastener 80 such that the anchor 100 does not pierce the surgical material 250. In some embodiments, when the surgical material 250 is not pierced by the anchor 100, the surgical material 250 is held and maintained between the interior face 11 of the first member 10 and the interior face 21 of the second member 20 by the tension between the anatomical structure and anchor 100 of surgical fastener 80. In alternative embodiments, additional engagement elements, for example a first engagement element 40 pin and a second engagement element 50 blind hole may secure the surgical material within the surgical fastener 80.

Surgical Fastener with Free Anchor

Figure 4A:
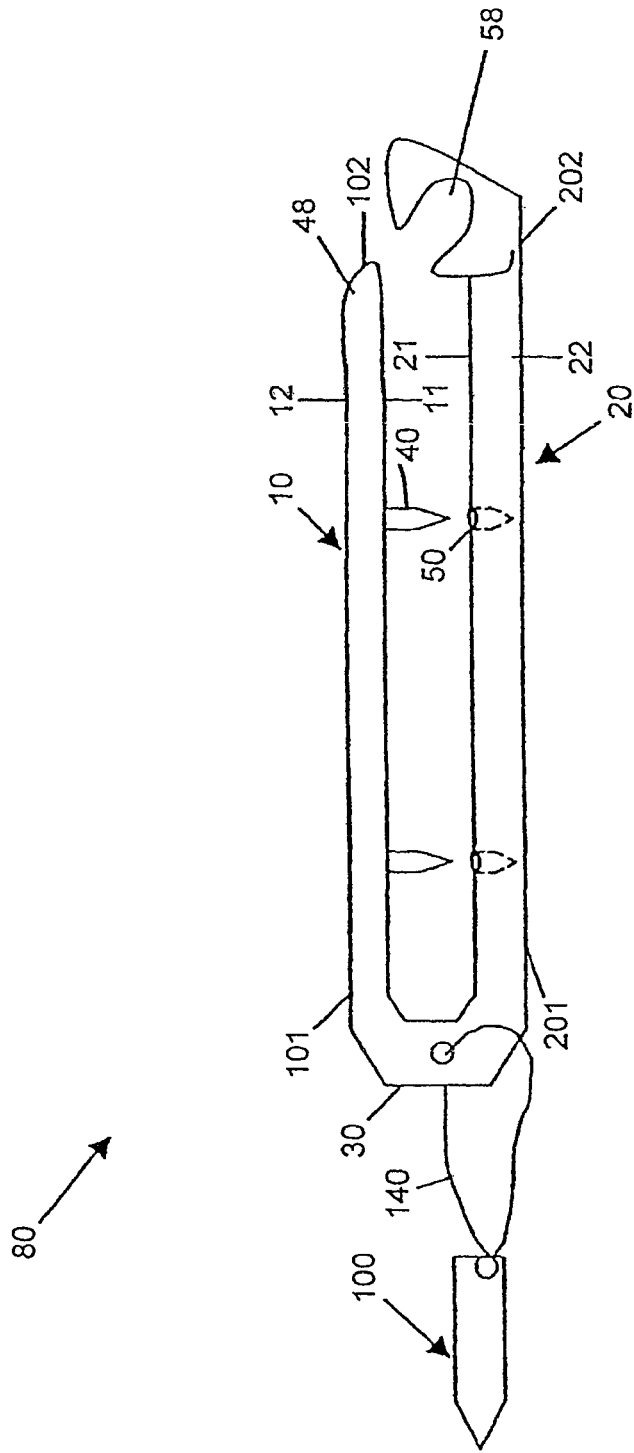
FIG. 4A is a longitudinal section of another embodiment of a surgical fastener including a free anchor attached by a flexible tether, in accordance with the present invention.

In another embodiment according to the invention, shown in FIG. 4A, the surgical fastener 80 further includes a flexible tether 140. The flexible tether 140 may be attached to the first member 10, the second member 20, or hinge section 30. In a particular embodiment, the flexible tether 140 is attached to either the proximal end 101 or the distal end 102 of the first member 10 or the flexible tether 140 is attached to the proximal end 201 or the distal end 202 of the second member 20. Alternatively, the flexible tether 140 is coupled within the surgical fastener 80 by a coupled first engagement element 40 and second engagement element 50.

The embodiment depicted in FIG. 4A illustrates a surgical fastener 80 with the anchor 100 attached by the flexible tether 140 to the hinge section 30. Thus, according to this embodiment of the invention, the anchor 100 is not attached to the first member 10 or the second member 20.

Figure 4B:
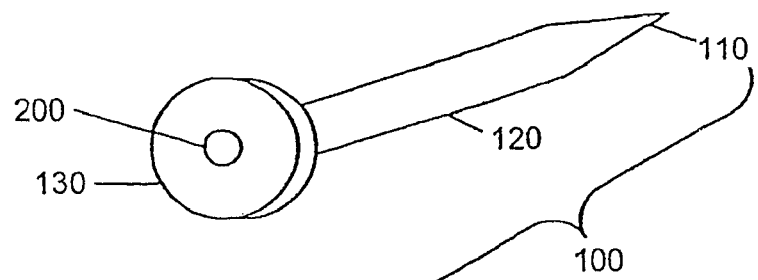
FIGS. 4B to 4D is a plan view of another embodiment of a surgical fastener with free anchor including a first engagement element pin and second engagement element aperture, in accordance with the present invention.
Figure 4C:
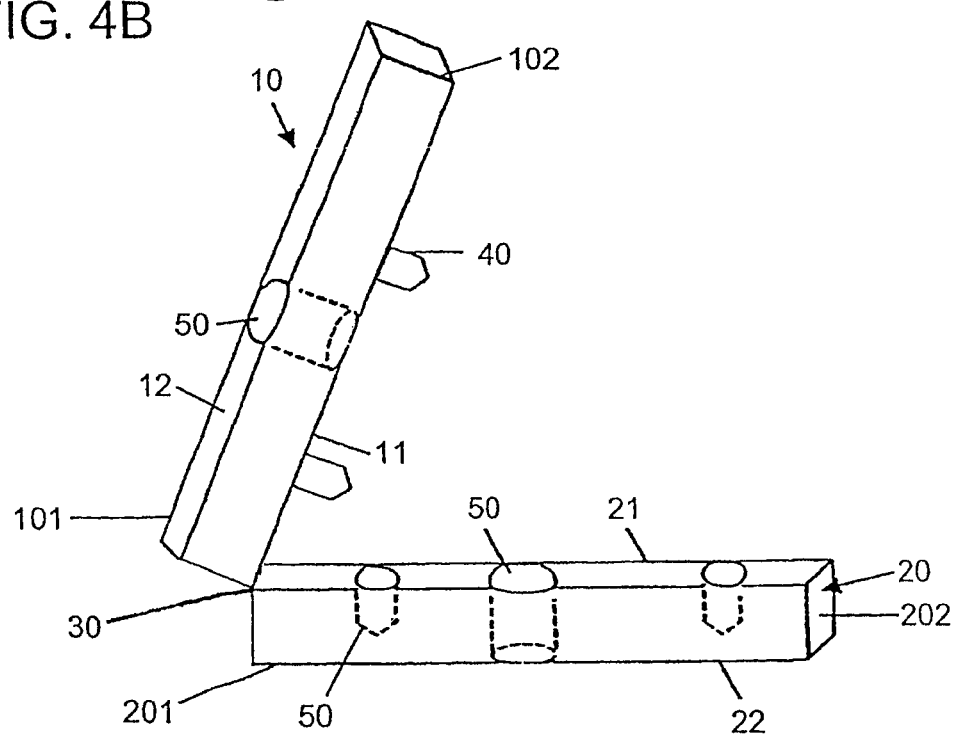
Figure 4D:
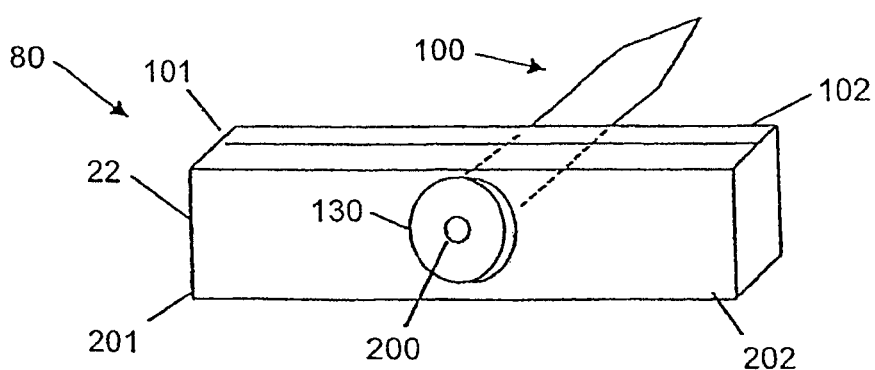

FIGS. 4B to 4D illustrate a schematic view of another embodiment of the surgical fastener according to the invention including a first member 10, a second member 20, a hinge section 30, and a free anchor 100. In this embodiment of the surgical fastener 80, referring to FIG. 4C, the first member 10 defines an aperture 50 that extends through member 10, and the second member 20 defines an aperture 50 that extends through member 20. When the first member 10 and the second member 20 are placed in the closed position, illustrated in FIG. 4D, the apertures 50 located on each member, 10 and 20, are aligned and define an opening through surgical fastener 80 from the exterior face 22 of the second member 20, to the exterior face 12 of the first member 10. Anchor 100, best illustrated in FIG. 4B, comprises a base 130, a shank 120, and a tapered head 110. The apertures 50 through first member 10 and the second member 20 of surgical fastener 80 and the base 130 are configured so that only the tapered head 110 and the shank 120 pass through the aperture 50 that extends through the surgical fastener 80. In a preferred embodiment, base 130 of anchor 100 features an implantation device attachment site 200 to facilitate releasable attachment of a detachable surgical anchor implantation device (not shown).

In the embodiment of the surgical fastener 80 illustrated in FIGS. 4B to 4D, the first member 10 features aperture 50 as the first engagement element 40, the second, member 20 features an aperture 50 as the second engagement element and the free anchor 100 functions as a third engagement element. Alternative surgical fasteners 80 feature both the first member 10 and the second member 20 but do not feature a hinge section 30 (not shown).

The surgical fastener 80 may be coupled in the closed position between an anatomical structure and base 130 by the anchor 100. In alternative embodiments, other engagement elements, for example a first engagement element 40 and a second engagement element 50 are employed to couple the surgical fastener 80 transitioning the surgical fastener 80 into the closed position. Exemplary first engagement elements 40 and second engagement elements 50 are: a pin and a blind hole, a pin and an aperture, a ridge and a groove, and a tongue 48 and a notch 58. In yet another embodiment, when the surgical fastener 80 is irreversibly coupled, the first member 10 and the second member 20 may, for example, be maintained in proximity and in the closed portion.

Surgical Fastener System

Figure 5A:
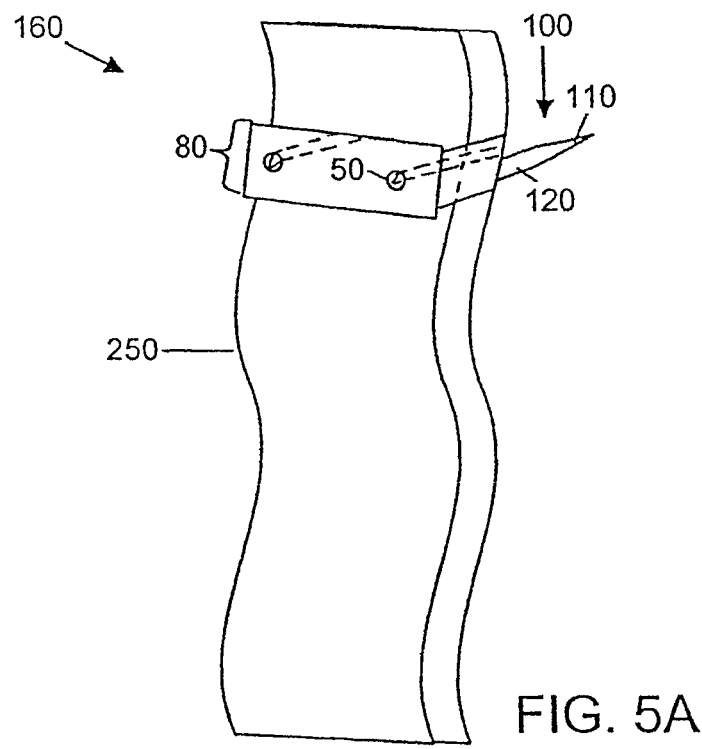
FIG. 5A is a plan view of an embodiment of a surgical fastener system with integral anchor, in accordance with the present invention.

In another aspect, the invention is a surgical fastener system 160. In one embodiment, shown in FIG. 5A the surgical fastener system includes the surgical fastener 80 with the anchor 100, and surgical material 250. The surgical fastener is similar to the surgical fastener 80 illustrated in FIG. 1F. In these embodiments shown in FIG. 5A, the pin 40 extends part way through the aperture 50, leaving a portion of the aperture 50 unfilled. The surgical fastener system 160 is secured to an anatomical structure by the anchor 100. Some or all of the tapered head 110 present at the distal end of anchor 100 is implanted into an anatomical structure. A portion of shank 120, located between a member of surgical fastener 80 and tapered head 110, may also be implanted into the anatomical structure. The anatomical structure that is the site of anchor implantation may be cartilage, tissue, muscle, or ligament. In a particular embodiment, the anchor 100 is implanted into bone.

Surgical Fastener System with Free Anchor

Figure 5B:
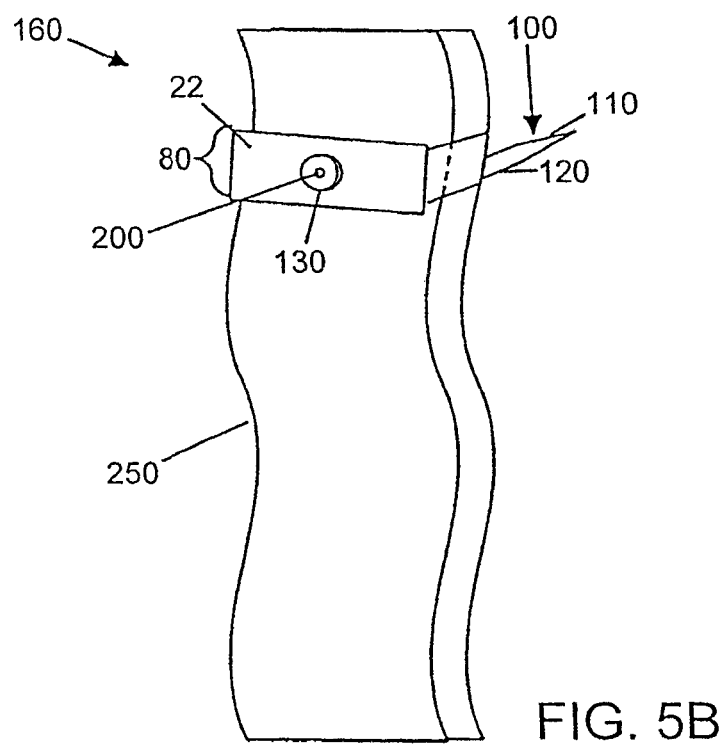
FIG. 5B is a plan view of an embodiment of a surgical fastener system with free anchor, in accordance with the present invention.

FIG. 5B provides a schematic view of another embodiment of a surgical fastener system 160, employing the surgical fastener 80 including a free anchor illustrated in FIGS. 4B and 4D, in accordance with the present invention. In this embodiment, the surgical fastener system 160 includes a surgical fastener 80 with a free anchor 100, and surgical material 250.

Surgical fastener systems 160 can be used to anchor surgical material 250 to anatomical structures. Preferable surgical materials 250 held within the surgical fastener 80 include slings, sutures, meshes, yarns, tapes, threads, grafts, fabrics, and sheaths. The surgical materials 250 are held within surgical fastener 80 by one or more combinations of coupled first engagement elements 40 and second engagement elements 50. Non limiting examples of coupled first and second engagement elements employed to secure surgical materials include: pins and cavities, pins and apertures, ridges and grooves, tongues and notches, and anchors and apertures.

Method of Surgical Fastener Use

Figure 6A:
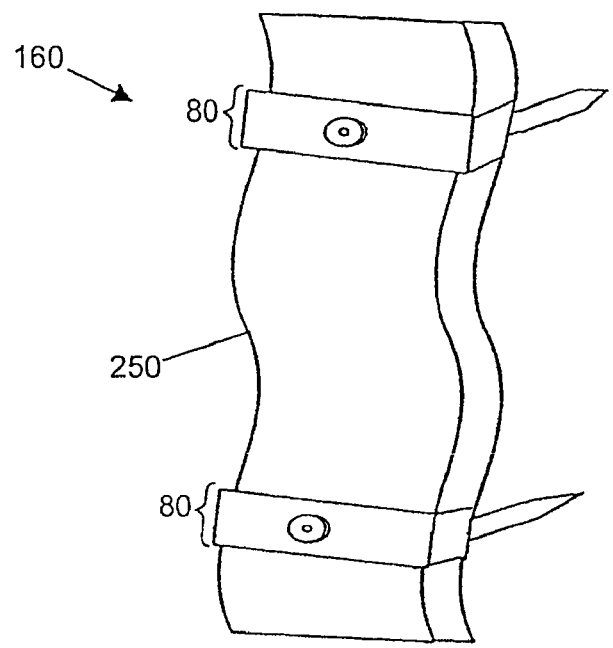
FIGS. 6A and 6B illustrate a surgical fastener system used in accordance with surgical methods of the present invention.
Figure 6B:
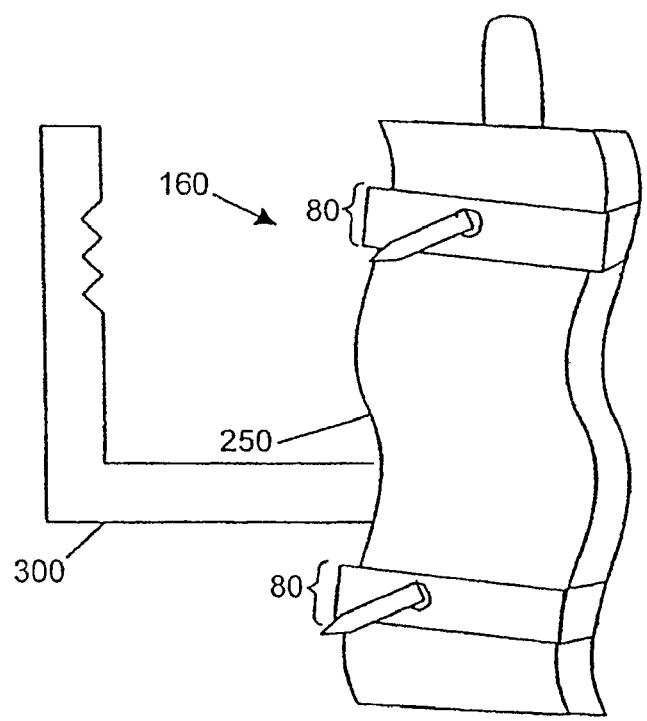
Figure 6C:
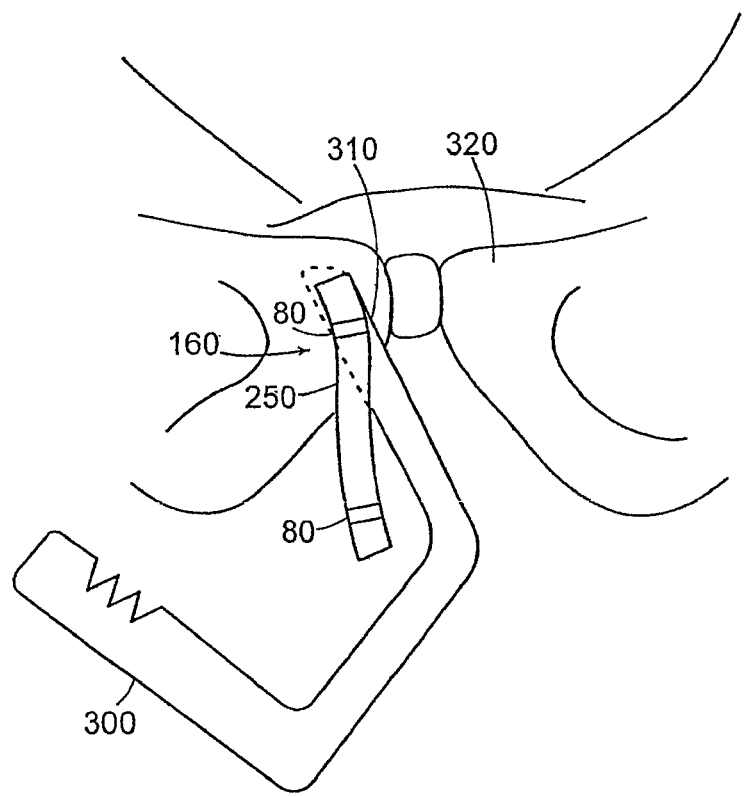
FIG. 6C to 6G illustrate methods of employing the surgical fastener system of FIGS. 6A and 6B to treat urinary incontinence.
Figure 6D:
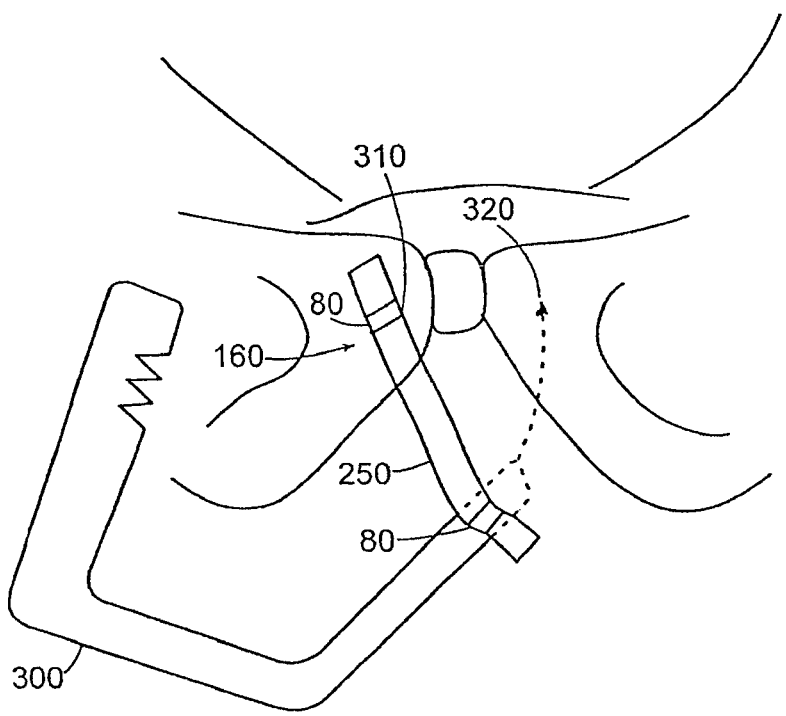
Figure 6E:
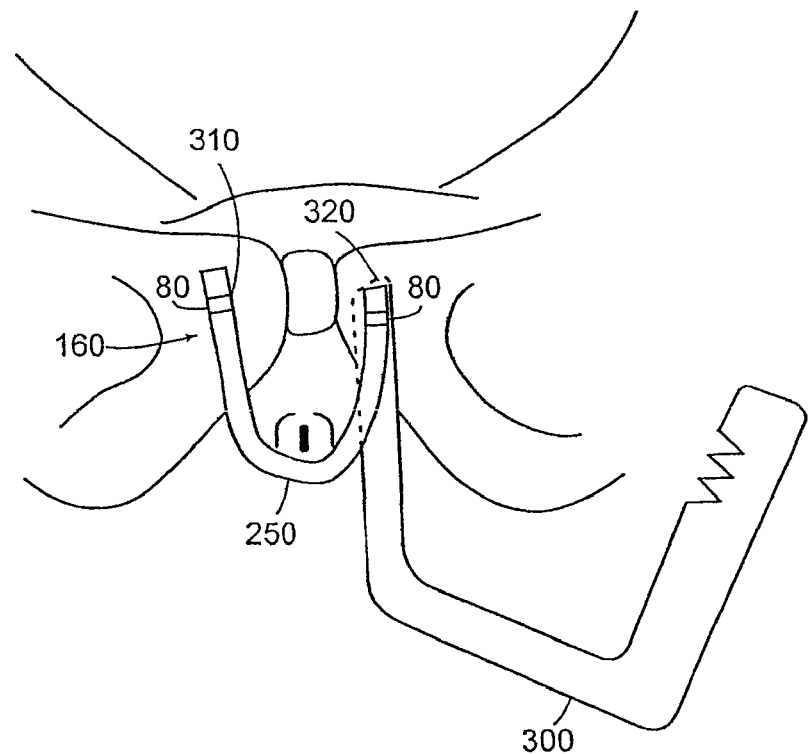
Figure 6F:
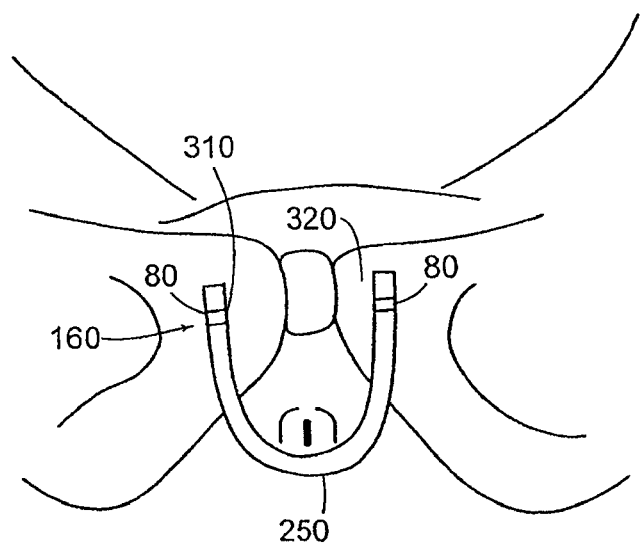
Figure 6G:
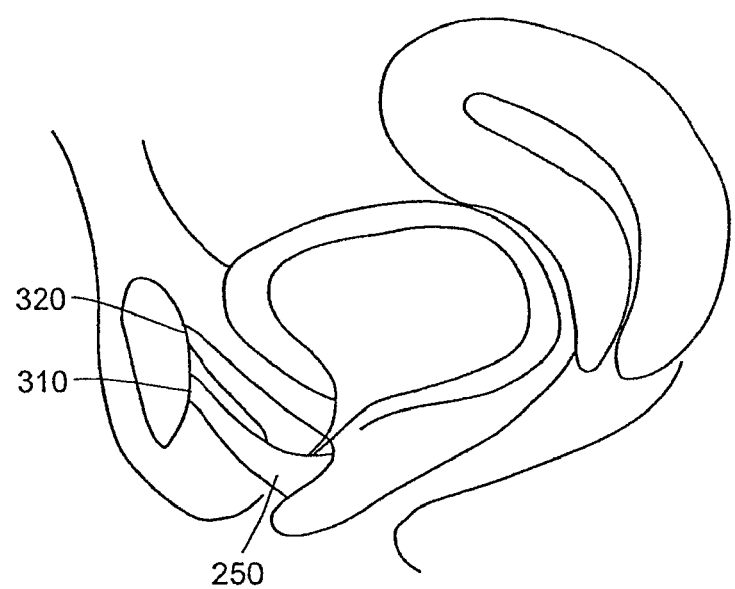

FIGS. 6A-6G diagramatically illustrate an embodiment according to the invention for securing a surgical fastener system 160 to an anatomical structure to treat stress female urinary incontinence surgery. In general overview, the method includes the steps of providing at least one surgical fastener 80 each comprising an anchor 100, as illustrated in conjunction with FIGS. 5A, 5B, and FIG. 6A, securing a first surgical fastener 80 to a detachable surgical anchor implantation device 300 (FIG. 6B), implanting the first surgical fastener 80 at the first anatomical structure implantation site 310 (FIG. 6C), securing a second surgical fastener 80 in the detachable surgical anchor implantation device 300 (FIG. 6D), implanting the second surgical fastener 80 at the second anatomical structure implantation site 320 (FIG. 6E), and confirming positioning of the surgical material 250 and the surgical faster(s) 80 of the surgical fastener system 160 at the first and second anatomical structure implantation sites 310 and 320 (FIGS. 6F and 6G).

More specifically, in one embodiment, illustrated in FIGS. 6A-6G, of the method according to the invention for implanting a surgical fastener at an implantation site in a body, the steps include providing a first and a second surgical fastener 80 (see FIGS. 4B to 4D and 5B) each comprising a first member 10 and a second member 20 and an anchor 100. The surgeon selects the appropriate size surgical material 250 depending on the patient's anatomy and on the surgical application. The surgical material 250 is positioned within surgical fastener 80 on top of the first member 10 and a first engagement element 40. The surgical fastener 80 is placed in the closed position securing the proximal end of surgical material 250 between the coupled first engagement element 40 and second engagement element 50.

The surgeon secures the distal end of surgical material 250 through a second surgical fastener 80. The length of surgical material 250 that the surgeon employs between the two surgical fasteners 80 will depend upon the surgical application. The surgical material 250 and the two surgical fasteners 80 are an embodiment of the surgical fastener system 160 of the invention. In one embodiment, a detachable surgical anchor implantation device 300 is releasably attached, illustrated in FIG. 6B, to the base 130 of the anchor 100 of the surgical fastener 80 that is secured at one end of the surgical material 250, see also FIG. 5B. The anchor 100 of the first surgical fastener 80 of the surgical fastener system 160 is implanted at a first anatomical implantation site 310 in the body of the patient, illustrated in FIG. 6C. The detachable surgical implantation device 300 is released from the anchor 100 and then releasably attached to the base 130 of a second anchor 100 of a second surgical fastener 80 secured to the opposite end of the surgical material 250, illustrated in FIG. 6D. The second anchor 100 of the second surgical fastener 80 of the surgical fastener system 160 is implanted at a second anatomical implantation site 320 inside the body of the patient, illustrated in FIG. 6E. The detachable surgical implantation device 300 is released from the second surgical fastener 80 and the detachable surgical implantation device 300 is withdrawn from the patient's body, illustrated in FIG. 6F. The surgical fastener system 160 including two surgical fasteners 80 and surgical material 250 remain in the patient's body illustrated in FIGS. 6F and 6G.

The surgical fastener of the present invention may be used in a plurality of surgical applications. Exemplary surgical applications utilizing these surgical fasteners include, without limitation, female stress urinary incontinence support surgery.

What is claimed is:

1. A surgical fastener, comprising:
    a proximal end and a distal end;
    a first member having a proximal end corresponding with the proximal end of the surgical fastener and a distal end corresponding with the distal end of the surgical fastener, the first member comprising a first interior face, a first exterior face, a first engagement element projecting from the first interior face at a first location between the proximal end of the surgical fastener and the distal end of the surgical fastener, and a tongue disposed at the distal end of the first member;
    a second member having a proximal end corresponding with the proximal end of the surgical fastener and a distal end corresponding with the distal end of the surgical fastener, the second member comprising a second interior face, a second exterior face, a second engagement element, the second engagement element complementary with the first engagement element at the first location between the proximal end of the surgical fastener and the distal end of the surgical fastener, and a notch disposed at the distal end of the second member, wherein, when the tongue is fixedly place in the notch, the first engagement element interfits into the second engagement element and the first interior face of the first member and the second interior face of the second member are substantially fixed in proximity to each other;
    a hinge section wherein the hinge section joins the first member and the second member; and
    an anchor located at the proximal end of the surgical fastener, the anchor being configured to anchor the surgical fastener at an anatomical site.

2. The surgical fastener of claim 1, further comprising a flexible tether wherein the anchor is attached to the proximal end of the surgical fastener by the flexible tether.

3. The surgical fastener of claim 1, wherein the anchor includes a tapered head, a shank, and a base.

4. The surgical fastener of claim 1, further comprising a flexible tether wherein the anchor is attached to the hinge section by the flexible tether.

5. The surgical fastener of claim 1, wherein the first engagement element comprises one or more pins positioned on the interior face of the first member; and the second engagement element is configured to couple with the one or more pins positioned on the first member, and wherein the second engagement element comprises the second member defining a blind hole.

6. The surgical fastener of claim 1, wherein the first engagement element comprises pin and the second engagement element comprises an aperture defined in the second member.

7. The surgical fastener of claim 1, wherein the first member further comprises another first engagement element and the second member further comprises another second engagement element.

8. The surgical fastener of claim 7, wherein the other first engagement element comprises a pin and the other second engagement element comprises an aperture defined in the second member.

9. The surgical fastener of claim 7, wherein the other first engagement element comprises a pin and the other second engagement element comprises the second member defining a blind hole.

* * * * *